United States Patent
Avakian

[11] 3,985,032
[45] Oct. 12, 1976

[54] MICROPIPETTE FILTER TIPS

[75] Inventor: Souren Avakian, Westport, Conn.

[73] Assignee: Centaur Chemical Co., Stamford, Conn.

[22] Filed: Nov. 13, 1975

[21] Appl. No.: 631,847

[52] U.S. Cl. .............................. 73/425.4 P; 23/292
[51] Int. Cl.² .......................................... B01L 3/02
[58] Field of Search ................... 73/425.4 P, 425.6; 23/253, 259, 292

[56] References Cited
UNITED STATES PATENTS

| | | | |
|---|---|---|---|
| 3,430,497 | 3/1969 | Tenczar | 73/425.6 |
| 3,449,081 | 6/1969 | Hughes | 73/425.6 |
| 3,846,077 | 11/1974 | Ohringer | 73/423.6 |

*Primary Examiner*—S. Clement Swisher
*Attorney, Agent, or Firm*—Buckles and Bramblett

[57] ABSTRACT

A removable, disposable molded plastic tip for use with a spring-loaded plunger-actuated vacuum pipette. The discharge end of the tip is provided with a solid porous filter member designed to filter a sample fluid during either of fluid entry into, or discharge from, the tip.

10 Claims, 6 Drawing Figures

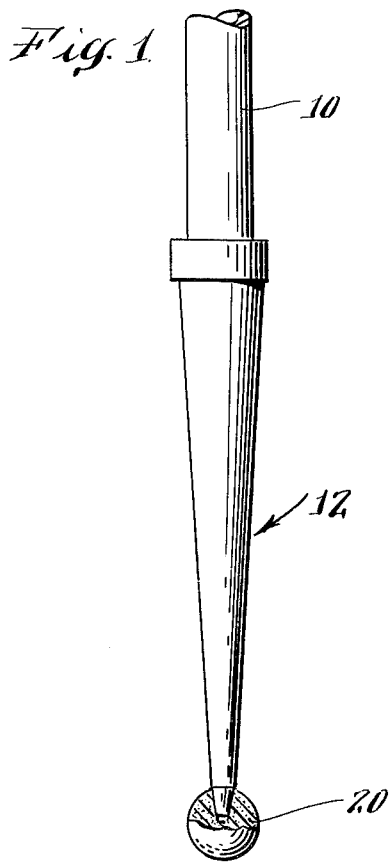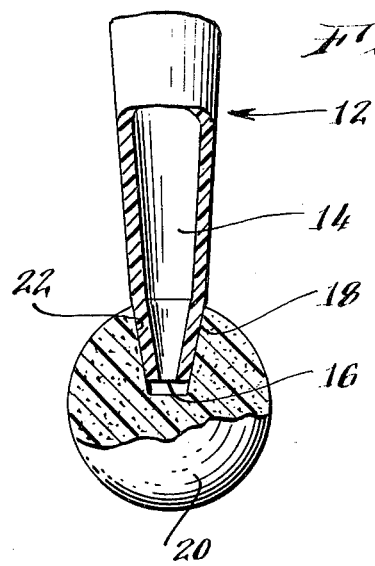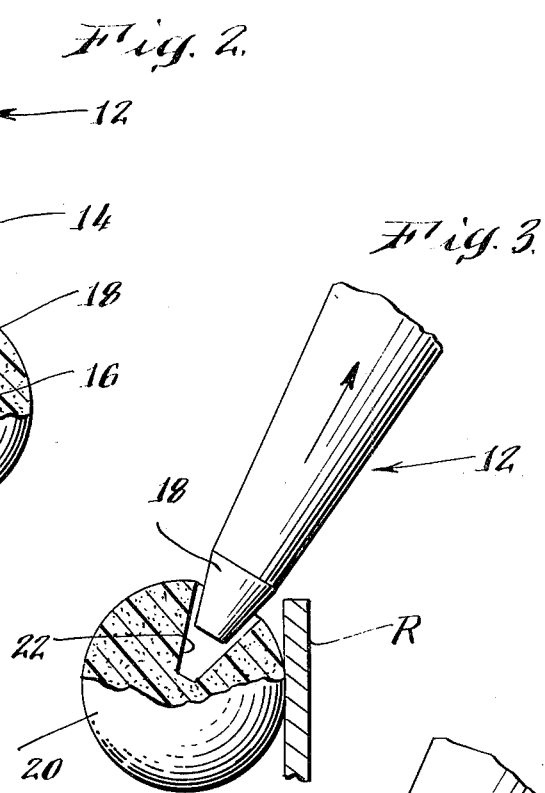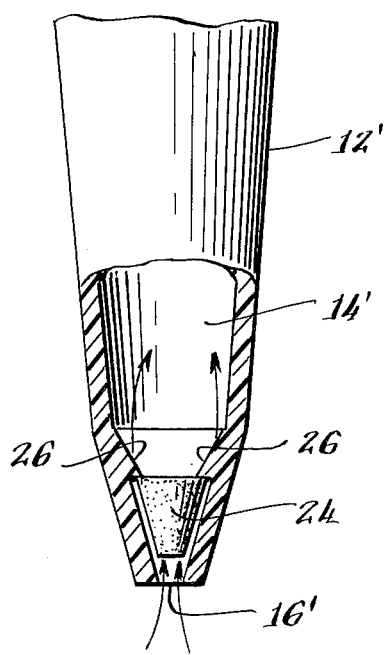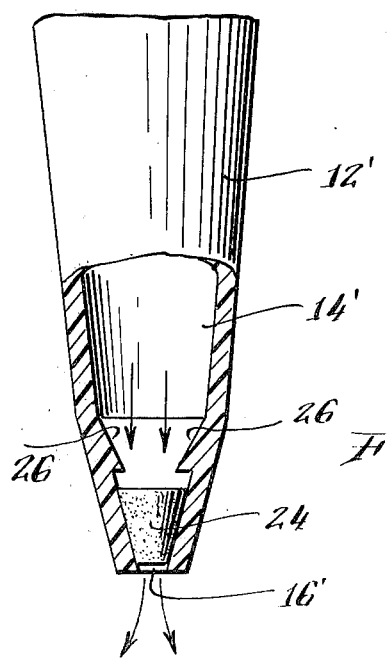

MICROPIPETTE FILTER TIPS

BACKGROUND OF THE INVENTION

In busy chemical and pharmaceutical laboratories it is often desirable to quickly and accurately measure and deliver microvolumes of various reagents and samples for analysis. For this purpose, various vacuum pipettes have been developed in the prior art. These pipettes are quite commonly used in conjunction with disposable tips formed of injection molded plastic material such as polyethylene. Such a tip is disclosed, for example, in U.S. Pat. No. 3,732,734 issued May 15, 1973 to the present inventor. These tips are easily and quickly inserted on the ends of pipette tubes with which they form an air tight seal and are thereafter easily and quickly removable for disposal after use. Such disposability eliminates the need for sterilization between samples. The pipettes and tips known to the prior art serve only as measuring and delivering means and the fluids which are sampled and measured remain substantially unaffected.

OBJECTS OF THE INVENTION

It is an object of the present invention to provide a disposable tip for a micropipette which has incorporated therein a device for filtering the fluid sample. Another object is to provide such a tip wherein filtering takes place either during entrance or discharge of the liquid sample to permit the discharge of a filtered sample. Other objects, features and advantages will become apparent from the following description and appended claims.

BRIEF DESCRIPTION OF THE DRAWING

For a fuller understanding of the nature and objects of the invention, reference should be had to the following detailed description in conjunction with the accompanying drawing wherein:

FIG. 1 is an elevational view, partially in cross section, of a tip and filter in accordance with the present invention;

FIG. 2 is an enlarged illustration, partially broken away, of a portion of the tip and filter of FIG. 1;

FIG. 3 is an enlarged illustration, partially in cross section, showing the removal of the filter of FIGS. 1 and 2 from the tip;

FIG. 4 is an illustration showing the discharge of filtered sample from the tip;

FIG. 5 is an illustration, partially broken away, of a modified version of a tip and filter in accordance with this invention during entrance of a sample fluid into the tip; and FIG. 6 is an illustration similar to FIG. 5 illustrating the discharge of a sample fluid through the filter.

DESCRIPTION OF THE PREFERRED EMBODIMENTS

With particular reference to FIG. 1, there is illustrated the nozzle 10 of a micropipette upon which is mounted a plastic tip member 12 which may be, for example, the type described in the above-referenced U.S. Pat. No. 3,732,734. Tip member 12 is conical in form and, as shown in FIG. 2, defines an internal axial passageway 14 which terminates at a fluid opening 16. The tip member 12 which is illustrated terminates at a distal portion 18 having a more pronounced conical angle than the main body portion of the tip 12. However, this is not a necessary feature of the invention.

Mounted upon the end of the tip member 12 is a filter 20 which may be made from any suitable material such as porous glass, porous plastic, or porous metal, such as a sintered metal. Some non-solids, such as stretchable polyurethanes, may also be used. The filter 20 is shown as spherical although this is not a limiting shape and any desired shape may be employed. Filter 20 defines a conical recess 22 which has a taper matching that of distal portion 18 of the tip member 12. The tip member 12 is inserted into the recess 22 so that the filter 20 is retained by means of friction.

In operation, the filter 20 and the tip of the tip member 12 is inserted into the liquid to be sampled. The plunger of the pipette is then depressed and released causing a measured amount of liquid sample to be drawn through the filter 20 and into the passageway 14 of the tip member 12. During this process, the sample liquid is filtered so that only filtered liquid enters the passageway 14. Thereafter, the filter 20 is removed by any suitable means such as, for example, engaging it with the rim R of a cup or other suitable receptacle as shown in FIG. 3. When the plunger of the pipette is thereafter depressed, there emerges from the tip member 12 only filtered sample S as shown in FIG. 4.

A variation of the invention is illustrated in FIGS. 5 and 6. In this modification, a conical filter 24 is mounted inside the tip member 12'. In order to retain the filter 24 adjacent the opening 16' of the tip member, there are provided a pair of inwardly extending projections 26 which are sufficiently resilient to permit the filter 24 to be pushed past them during assembly.

In the modification of FIGS. 5 and 6, the filter 24 functions in much the same manner as a check valve. Upon initial release of the pipette piston, sample fluid is inducted into the passageway 14', lifting the filter 24 in the process and flowing around it. Upon depressing the piston to discharge the sample, the filter 24 seats in the tip of the tip member 12' to seal opening 16', thereby forcing the sample liquid to pass through the filter 24 to be delivered in filtered form.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of the following claims.

I claim:

1. Filter apparatus for use with a liquid sampling pipette comprising: a detachable and disposable tip member in the form of a truncated hollow cone defining an axial passage therethrough; an opening defined by the truncated tip of said cone and communicating with said passage to receive the entrance and discharge cycle of liquid sample therethrough; and a porous filter positioned at said tip to close said opening during half of said entrance and discharge cycle and displaceable therefrom for the other half of said cycle.

2. The apparatus of claim 1 wherein said filter defines a recess for receiving and frictionally engaging said tip member.

3. The apparatus of claim 2 wherein said recess is conical with a taper substantially matching that of said tip.

4. The apparatus of claim 2 wherein said filter is of porous plastic.

5. The apparatus of claim 2 wherein said filter is of porous metal.

6. The apparatus of claim 1 wherein said filter is disposed within the axial passage defined by said tip and is movable by liquid entering said opening from a first position closing said opening to a second position displaced from said opening.

7. The apparatus of claim 6 wherein said axial passage includes at least one inwardly extending projection positioned to prevent movement of said filter beyond said second position.

8. The apparatus of claim 6 wherein said filter is conical with a taper substantially matching that of said passage adjacent said opening.

9. The apparatus of claim 8 wherein said filter is of porous plastic.

10. The apparatus of claim 8 wherein said filter is of porous metal.

* * * * *